US012745730B2

(12) United States Patent
Krouse

(10) Patent No.: US 12,745,730 B2
(45) Date of Patent: Sep. 29, 2026

(54) ***CANNABIS* HYBRID ADAM**

(71) Applicant: James Krouse, Beverly Hills, CA (US)

(72) Inventor: James Krouse, Beverly Hills, CA (US)

( * ) Notice: Subject to any disclaimer, the term of this patent is extended or adjusted under 35 U.S.C. 154(b) by 344 days.

(21) Appl. No.: 18/327,416

(22) Filed: Jun. 1, 2023

(65) Prior Publication Data

US 2023/0389500 A1 Dec. 7, 2023

Related U.S. Application Data

(60) Provisional application No. 63/365,792, filed on Jun. 3, 2022.

(51) Int. Cl.
*A01H 5/10* (2018.01)
*A01H 6/28* (2018.01)

(52) U.S. Cl.
CPC ................. *A01H 6/28* (2018.05); *A01H 5/10* (2013.01)

(58) Field of Classification Search
None
See application file for complete search history.

(56) References Cited

U.S. PATENT DOCUMENTS

| | | | | |
|---|---|---|---|---|
| 9,095,554 | B2 | 8/2015 | Lewis | |
| 10,888,059 | B1 * | 1/2021 | Reel | A01H 5/02 |
| 11,240,978 | B2 | 2/2022 | Frazier | |
| 2017/0339907 | A1 | 11/2017 | Fletcher | |
| 2020/0267920 | A1 | 8/2020 | Stanley | |

FOREIGN PATENT DOCUMENTS

| | | |
|---|---|---|
| WO | 2023235801 | 12/2023 |

OTHER PUBLICATIONS

USDA, “Applying for a Plant Variety Certificate of Protection”, https://www.ams.usda.gov/services/pvpo/application-help/apply, accessed May 1, 2023.*

UPOV, 2017, Explanatory Notes on Essentially Derived Varieties Under the 1991 Act of the UPOV Convention.*

Ex Parte C (USPQ 2d 1492 (1992).*

Ex Parte McGowen—Board Decision in U.S. Appl. No. 14/996,093. (Year: 2020).*

Huan et al. Plant Physiology. 155:645-655. (Year: 2011).*

Großinsky et al. Journal of Experimental Botany. 66(18):5429-5440. (Year: 2015).*

International Search Report (ISR) for PCT/US 23/67760 filed on Jun. 1, 2023, Date of completion of the ISR: Sep. 7, 2023; Date of mailing of the ISR: Oct. 3, 2023).

McPartland, J.M. and Small, E., “A classification of endangered high-THC *Cannabis* (*Cannabis sativa* subsp. *indica*) domesticates and their wild relatives,” PhytoKeys, 144: 81-112 (2020).

* cited by examiner

*Primary Examiner* — David R Byrnes
(74) *Attorney, Agent, or Firm* — Saul Ewing LLP

(57) ABSTRACT

The invention relates to the *Cannabis* hybrid designated ADAM. Provided by the invention are the seeds, plants and derivatives of the *Cannabis* hybrid ADAM. Also provided by the invention are tissue cultures of the *Cannabis* hybrid ADAM and the plants regenerated therefrom. Still further provided by the invention are methods for producing *Cannabis* plants by crossing the *Cannabis* hybrid ADAM with itself or another *Cannabis* plant, and plants produced by such methods.

11 Claims, No Drawings

*CANNABIS* HYBRID ADAM

CROSS-REFERENCE TO RELATED APPLICATIONS

This application claims benefit of U.S. Provisional Application No. 63/365,792, filed Jun. 3, 2022, which is incorporated herein by reference in its entirety.

FIELD OF THE INVENTION

The present invention relates generally to the field of *Cannabis* plants. In particular, the invention relates to the novel *Cannabis* hybrid ADAM.

BACKGROUND OF THE INVENTION

Much of modern "medical *Cannabis*" has hemp in its genetics. While hemp has many uses, it is believed that its fiber strains should not be part of *Cannabis* plants that are bred for medical use. The presence of hemp DNA in commercial *Cannabis* may also introduce problems into the growing process such as, for example, rust fungi. Further, since farmers have bred their redundant hybrids with hemp in hopes to regain yield, many of today's *Cannabis* genomes are interrelated and there is practically little or no difference genetically between today's "hemp" and "marijuana" genetics. Indeed, most *Cannabis* on today's market has been excessively hybridized, mutated, and self-ed leading to a large reduction in yield and the expression of undesirable characteristics.

There is a need to develop *Cannabis* plants that have the traits that result in superior hybrids and varieties.

SUMMARY OF THE INVENTION

In one aspect, the present invention provides a plant of *Cannabis* hybrid ADAM, wherein representative seed of said hybrid have been deposited with the American Type Culture Collection (ATCC) under ATCC Accession No. PTA-127583.

In another aspect, the present invention provides a seed of *Cannabis* hybrid ADAM.

In some aspects, the present invention provides a method of producing a *Cannabis* seed, the method comprising crossing the plant of plant of *Cannabis* hybrid ADAM with itself or a second *Cannabis* plant to produce said *Cannabis* seed.

In other aspects, the present invention provides an $F_1$ *Cannabis* seed produced by crossing the plant of plant of *Cannabis* hybrid ADAM with itself or a second *Cannabis* plant to produce said *Cannabis* seed.

In one aspect, the present invention provides an $F_1$ *Cannabis* plant produced by growing the $F_1$ *Cannabis* seed produced by crossing the plant of plant of *Cannabis* hybrid ADAM with itself or a second *Cannabis* plant to produce said *Cannabis* seed.

In another aspect, the present invention provides a composition comprising the seed of seed of *Cannabis* hybrid ADAM or the $F_1$ *Cannabis* seed comprised in plant seed growth media.

In some aspects, the present invention provides a plant of *Cannabis* hybrid ADAM further comprising a single locus conversion, wherein said plant otherwise comprises all of the morphological and physiological characteristics of said *Cannabis* hybrid ADAM.

In other aspects, the present invention provides a seed that produces the plant of *Cannabis* hybrid ADAM further comprising the single locus conversion.

In one aspect, the present invention provides a method of producing a commodity plant product, the method comprising producing the commodity plant product from the plant of *Cannabis* hybrid ADAM or the plant of *Cannabis* hybrid ADAM further comprising the single locus conversion

DETAILED DESCRIPTION

In one aspect, the present invention provides a plant of *Cannabis* hybrid ADAM, wherein representative seed of said hybrid have been deposited under ATCC Accession No. PTA-127583.

In one embodiment, a plant part of the plant of *Cannabis* hybrid ADAM is also provided, wherein the plant part comprises at least one cell of said plant of *Cannabis* hybrid ADAM.

In another aspect, the present invention provides a seed of *Cannabis* hybrid ADAM.

In other aspects, the present invention provides methods for crossing the *Cannabis* hybrid ADAM with itself or a second plant and the seeds and plants produced by such methods.

In some embodiments, a method of producing a *Cannabis* seed comprises crossing the plant of *Cannabis* hybrid ADAM with itself or a second *Cannabis* plant to produce said *Cannabis* seed.

These methods can be used for propagation of the *Cannabis* hybrid ADAM, or can be used to produce hybrid *Cannabis* seeds and the plants grown therefrom. In some embodiments, hybrid *Cannabis* plants can be used in the production of *Cannabis* products or may be employed in certain breeding protocols to produce novel *Cannabis* hybrids or varieties. In other embodiments, a hybrid plant can also be used as a recurrent parent at any given stage in a backcrossing protocol e.g., during the production of a single locus conversion of the *Cannabis* hybrid ADAM.

Propagation and breeding of *Cannabis* is described in Robert C. Clarke, "*Marijuana Botany: An Advanced Study: The Propagation and Breeding of Distinctive Cannabis*," Ronin Publishing; 2nd ed. Edition; 197 pages (Jun. 15, 1981), which is herein incorporated by reference in its entirety. *Cannabis* domestication and breeding history is described in Robert C. Clarke & Mark D. Merlin, "*Cannabis Domestication, Breeding History, Present-day Genetic Diversity, and Future Prospects, Critical Reviews in Plant Sciences,*" 35:5-6, 293-327 (2016), which is herein incorporated by reference in its entirety. Descriptions of other breeding methods can be found in e.g., Robert W. Allard, "*Principles of Plant Breeding*," John Wiley & Sons, NY, University of California, Davis, Calif, 50-98 (1960) and Ed. J. Sneep and A. J. T. Hendriksen, "*Plant breeding perspectives*," Wageningen, The Netherlands: Centre Agricultural Publishing and Documentation (PUDOC), pp. 435 (1979), each of which is herein incorporated by reference in its entirety.

In other embodiments, in selecting a second plant to cross with *Cannabis* hybrid ADAM for the purpose of developing novel *Cannabis* hybrids and/or varieties, plants that either themselves exhibit one or more selected characteristics or that exhibit the characteristic(s) when in hybrid combination may be used in the cross. Examples of potentially selected characteristics include, but are not limited to, cannabinoid (e.g., tetrahydrocannabinol (THC), cannabidiol (CBD)) content, terpene content, flower to leaf ratio, yield of flowers, branching, size (e.g., shortened) of internodes, maturity, floral response to inductive photoperiods, seed yield, lodging tolerance, seedling vigor, disease tolerance, and/or plant height.

Choice of breeding or selection methods can depend on the mode of plant reproduction, the heritability of the trait(s) being improved, and the type of variety used commercially (e.g., $F_1$ hybrid variety, pureline variety, etc.). In some embodiments, examples of breeding methods can include cross-breeding, selfing, back-crossing, embryo rescue, in-crossing, out-crossing, inbreeding, selection, asexual propagation, and other traditional techniques as are known in the art. In other embodiments, selection methods can include pedigree selection, modified pedigree selection, mass selection, recurrent selection and backcrossing.

In some embodiments, backcross breeding is used to transfer one or a few genes for a highly heritable trait into a desirable variety. Various recurrent selection techniques are used to improve quantitatively inherited traits controlled by numerous genes.

In some embodiments, the goal of plant breeding is to develop new, unique, and superior *Cannabis* varieties and hybrids. In one embodiment, two or more parental lines can initially be selected and crossed. This is generally followed by repeated selfing and selection, which produces many new genetic combinations. For example, in one embodiment, the plant breeder can select the germplasm each growing cycle to advance to the next generation. This germplasm can be grown under unique and different geographical, climatic, and/or soil conditions, and further selections are then made during and at the end of the growing season.

In other embodiments, pedigree breeding is used. For example, two parents that possess favorable, complementary traits are crossed to produce $F_1$ progeny. An $F_2$ population is then produced by selfing one or several $F_1$ plants. Selection of the best individuals may begin in the $F_2$ population or later depending upon the objectives; then, beginning in the $F_3$ generation, the best individuals in the best families can be selected. Replicated testing of families can begin in the $F_3$ or $F_4$ generations to improve the effectiveness of selection for traits of low heritability. At an advanced stage of inbreeding (i.e., the $F_6$ and $F_7$ generations), the best lines or mixtures of phenotypically similar lines are tested for potential release as new varieties.

In another embodiment, mass and recurrent selections can be used e.g., to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population from which further cycles of selection are continued.

In other embodiments, backcross breeding has been used to transfer genetic loci for simply inherited or highly heritable traits into a homozygous variety that is used as the recurrent parent. The source of the trait to be transferred is called the donor or nonrecurrent parent. The resulting plant is expected to have the attributes of the recurrent parent and the trait transferred from the donor parent. After the initial cross, individuals possessing the phenotype of the donor parent are selected and repeatedly crossed, i.e., backcrossed, to the recurrent parent. The resulting plant is expected to have the attributes of the recurrent parent (i.e., variety) and the desirable trait transferred from the donor parent.

In some embodiments, a plant can be identified by its phenotype and/or genotype. In one embodiment, the genotype of a plant can be characterized through a molecular marker profile, which can identify plants of the same variety or a related variety, can identify plants and plant parts which are genetically superior because of an event e.g., an event comprising a backcross conversion, transgene, or genetic sterility factor, or can be used to determine or validate a pedigree. Such molecular marker profiling can be accomplished using a variety of techniques including, but not limited to, restriction fragment length polymorphism (RFLP), amplified fragment length polymorphism (AFLP), sequence-tagged sites (STS), randomly amplified polymorphic DNA (RAPD), arbitrarily primed polymerase chain reaction (AP-PCR), DNA amplification fingerprinting (DAF), sequence characterized amplified regions (SCARs), variable number tandem repeat (VNTR), short tandem repeat (STR), single feature polymorphism (SFP), simple sequence length polymorphism (SSLP), restriction site associated DNA, allozymes, isozyme markers, single nucleotide polymorphisms (SNPs), or simple sequence repeat (SSR) markers, also known as microsatellites. Various types of these markers, for example, can be used to identify individual varieties developed from specific parent varieties, as well as cells or other plant parts thereof.

In some embodiments, one or more markers may be used to characterize and/or evaluate a *Cannabis* variety. Markers used for these purposes are not limited to any set of markers but can include any type of marker and marker profile that provides a means for distinguishing varieties. One method of comparison may be to use only homozygous loci for *Cannabis* hybrid ADAM.

Molecular makers for *Cannabis* plants are described in U.S. Pat. No. 9,095,554, Datwyler et al., "*Genetic variation in hemp and marijuana* (*Cannabis sativa* L.) *according to amplified fragment length polymorphisms*," J Forensic Sci., 51(2):371-5 (2006), Pinarkara et al., "*RAPD analysis of seized marijuana* (*Cannabis sativa* L.) *in Turkey*," Electronic Journal of Biotechnology, 12(1) (2009), Hakki et al., "*Inter simple sequence repeats separate efficiently hemp from marijuana* (*Cannabis sativa* L.)," Electronic Journal of Biotechnology, 10(4) (2007), Datwyler et al., "*Genetic Variation in Hemp and Marijuana* (*Cannabis sativa* L.) *According to Amplifed Fragment Length Polymorphisms*," J Forensic Sci, 51(2):371-375 (2006), Gilmore et al., "*Isolation of microsatellite markers in Cannabis sativa* L. (*marijuana*)," Molecular Ecology Notes, 3(1):105-107 (2003), Pacifico et al., "*Genetics and marker-assisted selection of chemotype in Cannabis sativa* L.," Molecular Breeding, 17:257-268 (2006), and Mendoza et al., "*Genetic individualization of Cannabis sativa by a short tandem repeat multiplex system*," Anal Bioanal Chem, 393:719-726 (2009), each of which is herein incorporated by reference in its entirety.

In addition to being used for identification of *Cannabis* hybrid ADAM, as well as plant parts and plant cells of *Cannabis* hybrid ADAM, a genetic profile may be used to identify a *Cannabis* plant produced using *Cannabis* hybrid ADAM or to verify a pedigree for progeny plants produced using *Cannabis* hybrid ADAM. A genetic marker profile may also be useful in breeding and developing backcross conversions.

In one embodiment, the present invention provides a *Cannabis* plant characterized by molecular and physiological data obtained from a representative sample of said ADAM deposited with the ATCC under ATCC Accession No. PTA-127583. Thus, plants, seeds, or parts thereof, having all or substantially all the morphological and physiological characteristics of *Cannabis* hybrid ADAM are provided. Further provided is a *Cannabis* plant formed by the combination of the disclosed *Cannabis* plant or plant cell with another *Cannabis* plant or cell and comprising the homozygous alleles of the variety.

In some embodiments, a plant, a plant part, or a seed of *Cannabis* hybrid ADAM may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like. In some embodiments, a phenotypic profile can include increased or decreased production of THC, CBD, cannabigerol (CBG), tetrahydrocannabivarin (THCV), cannabichromene (CBC), and/or terpenes.

In some embodiments, genetic marker profiles are performed using SSR polymorphisms that are well known in the art. A marker system based on SSRs can be highly informative in linkage analysis relative to other marker systems, in that multiple alleles may be present. Another advantage of this type of marker is that through use of flanking primers, detection of SSRs can be achieved, for example, by using the polymerase chain reaction (PCR). PCR detection may be performed using two oligonucleotide primers flanking the polymorphic segment of repetitive DNA to amplify the SSR region.

Following amplification, markers can be scored by electrophoresis of the amplification products. Scoring of marker genotype is based on the size of the amplified fragment, which correlates to the number of base pairs of the fragment. While variation in the primer used or in the laboratory procedures can affect the reported fragment size, relative values should remain constant regardless of specific primer or laboratory used.

A genotypic profile of *Cannabis* hybrid ADAM can be used to identify a plant comprising hybrid ADAM as a parent, since such plants will comprise the same homozygous alleles as hybrid ADAM.

In other embodiments, plants and plant parts substantially benefiting from the use of hybrid ADAM in their development, such as hybrid ADAM comprising a backcross conversion, transgene, or genetic sterility factor, may be identified by having a molecular marker profile with a percent identity to *Cannabis* hybrid ADAM. In some embodiments, the percent identity is 90%, 91%, 92%, 93%, 94%, 95%, 96%, 97%, 98%, 99%, 99.5% or 99.9% identical to *Cannabis* hybrid ADAM.

In other embodiments, a genotypic profile of hybrid ADAM also can be used to identify essentially derived varieties and other progeny varieties developed from the use of hybrid ADAM, as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of hybrid ADAM when grown under the same conditions. Progeny plants and plant parts produced using hybrid ADAM may be identified, for example, by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from *Cannabis* hybrid ADAM, as measured by either percent identity or percent similarity. Such progeny may be further characterized as being within a pedigree distance of hybrid ADAM, such as within 1, 2, 3, 4, or 5 or less cross pollinations to a *Cannabis* plant other than hybrid ADAM, or a plant that has hybrid ADAM as a progenitor. Unique molecular profiles may be identified with other molecular tools, such as SNPs and RFLPs.

Any time the *Cannabis* hybrid ADAM is crossed with another, different, variety, first generation ($F_1$) *Cannabis* progeny are produced. The hybrid progeny are produced regardless of characteristics of the two varieties produced. As such, an $F_1$ hybrid *Cannabis* plant may be produced by crossing ADAM with any second *Cannabis* plant. In one embodiment, the second *Cannabis* plant may be genetically homogeneous (e.g., inbred) or may itself be a hybrid. Therefore, any $F_1$ hybrid *Cannabis* plant produced by crossing *Cannabis* hybrid ADAM with a second *Cannabis* plant is a part of the present invention.

In other embodiments, hand pollination is used by crossing of plants via the deliberate fertilization of female ovules with pollen from a desired male parent plant. In some embodiments the donor or recipient female parent and the donor or recipient male parent line are planted in the same field. The inbred male parent can be planted earlier or later than the female parent to ensure adequate pollen supply at the pollination time. In some embodiments, the male parent and female parent can be planted at a ratio e.g., a ratio of 1 male parent to 2-6 female parents. For example, the male parent may be planted at the top of the field for efficient male pollen collection during pollination. Pollination is started when the female parent flower is ready to be fertilized and there is available pollen from the male parent. In some embodiments, the male pollen used for fertilization has been previously collected and stored.

In other embodiments, breeding schemes of the present invention can include crosses with targeting induced local lesions in genomes (TILLING) plant lines. TILLING is a method known in the art that allows directed identification of mutations in a specific gene. The method combines mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING techniques to look for natural mutations in individuals, usually for population genetics analysis (Comai, et al., The Plant Journal, 37:778-786 (2003); Gilchrist et al., Mol. Ecol., 15:1367-1378 (2006); Mejlhede et al., Plant Breeding, 125:461-467 (2006); and Nieto et al, BMC Plant Biology, 7:34-42 (2007)), each of which is herein incorporated by reference in its entirety). DEcoTILLING is a modification of TILLING and EcoTILLING which uses an inexpensive method to identify fragments (Garvin et al., "*DEco-TILLING: An inexpensive method for SNP discovery that reduces ascertainment bias.*" Molecular Ecology Notes, 7:735-746 (2007), which is herein incorporated by reference in its entirety).

The TILLING method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING or the natural mutation or SNP in EcoTILLING), they provoke a shape change in the double strand DNA fragment which is then cleaved by single stranded nucleases. The products are then separated by size on several different platforms. Other descriptions on methods and compositions on TILLING can be found in U.S. Pat. No. 5,994,075, US 2004/0053236 A1, WO 2005/055704, and WO 2005/048692, each of which is herein incorporated by reference in its entirety.

In other embodiments, mutation breeding is used for introducing new variation and subsequent traits into *Cannabis* plants. Mutations that occur spontaneously or are artificially induced can be useful sources of variability for the plant breeder. The goal of artificial mutagenesis is to increase the rate of mutation for a desired characteristic. Mutation rates can be increased by many different methods or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis, the trait may then be incorporated into existing germplasm by traditional breeding techniques.

In some embodiments, day length sensitivity is an important consideration when genotypes are grown outside of their area of adaptation. For examples, when genotypes adapted to tropical latitudes are grown in the field at higher latitudes, they may not mature before frost occurs. Plants can be induced to flower and mature earlier by creating artificially short days or by grafting.

In some embodiments, the light level required to delay flowering is dependent on the quality of light emitted from the source and the genotype being grown. For example, in one embodiment, blue light with a wavelength of about 480 nm can require more energy to inhibit flowering as red light with a wavelength of about 640 nm.

In other embodiments, the invention provides self-pollination populations whereby the pollen of one flower on one plant is applied (artificially or naturally) to the ovule (stigma) of the same or a different flower on the same plant.

In one embodiment, for the crossing of two *Cannabis* plants, artificial hybridization is used.

In artificial hybridization, the flower used as a female in a cross is manually cross pollinated prior to maturation of pollen from the flower, thereby preventing self-fertilization, or alternatively, the male parts of the flower are emasculated using a technique known in the art. Techniques for emasculating the male parts of a *Cannabis* flower include, for example, physical removal of the male parts, use of a genetic factor conferring male sterility, and application of a chemical gametocide to the male parts.

In other embodiments, the female flower is hand-pollinated.

In another aspect, the present invention provides a plant of *Cannabis* hybrid ADAM further comprising a single locus conversion, wherein said plant otherwise comprises all of the morphological and physiological characteristics of said *Cannabis* hybrid ADAM.

In some embodiments, a plant of *Cannabis* hybrid ADAM is modified to comprise a heritable trait. The heritable trait may comprise a genetic locus that is a dominant or recessive allele. In one embodiment, a plant of *Cannabis* hybrid ADAM comprises a single locus conversion. An added genetic locus which confers one or more traits such as, for example, male sterility, herbicide tolerance, tolerance to bacterial, fungal, or viral disease, insect and pest tolerance, restoration of male fertility, yield stability and/or enhancement, abiotic stress tolerance, and/or modified fatty acid metabolism is provided. The trait may be, for example, conferred by a naturally occurring *Cannabis* gene introduced into the genome of the variety by backcrossing, a natural or induced mutation, or a transgene introduced through genetic transformation techniques. In other embodiments, when introduced through transformation, a genetic locus may comprise one or more transgenes integrated at a single chromosomal location. In some embodiments, the single locus comprises a nucleic acid sequence that enables site-specific genetic recombination.

In some embodiments, such plants may be developed by a plant breeding technique called backcrossing, wherein essentially all the morphological and physiological characteristics of a hybrid ADAM are recovered in addition to a genetic locus transferred into the plant via the backcrossing technique. By essentially all the morphological and physiological characteristics, it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

In one embodiment of a backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a *Cannabis* plant is obtained, wherein essentially all the morphological and physiological characteristics of the recurrent parent are recovered in the converted plant, in addition to the transferred locus from the nonrecurrent parent.

In some embodiments, the goal of a backcross protocol is to alter or substitute a trait or characteristic in the original hybrid or variety. To accomplish this, in one embodiment, a locus of the recurrent hybrid or variety is modified or substituted with the desired locus from the nonrecurrent parent, while retaining essentially all of the rest of the genome of the original hybrid or variety, and therefore the morphological and physiological constitution of the original hybrid or variety. Although backcrossing methods are simplified when the characteristic being transferred is a dominant allele, a recessive allele may also be transferred. In this instance, it may be necessary to introduce a test of the progeny to determine if the desired characteristic has been successfully transferred.

In other embodiments, modified backcrossing is preformed using different recurrent parents during the backcrossing. Modified backcrossing may be used to replace the original recurrent parent with a variety having certain more desirable characteristics or multiple parents may be used to obtain different desirable characteristics from each.

Many traits have been identified that are not regularly selected for in the development of a new inbred but that can be improved by backcrossing techniques.

In one embodiment, direct selection may be applied when the locus acts as a dominant trait. An example of a dominant trait is the herbicide tolerance trait. For this selection process, the progeny of the initial cross are sprayed with the herbicide prior to the backcrossing. The spraying eliminates any plants which do not have the desired herbicide tolerance characteristic, and only those plants that have the herbicide tolerance gene are used in the subsequent backcross. This process is then repeated for all additional backcross generations.

In another embodiment, a suitable genetic marker that is closely associated with a trait of interest can be used for selection of *Cannabis* plants for breeding. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay that can identify the relative presence or absence of a trait of interest in a plant may also be useful for breeding purposes.

Many useful traits that can be introduced by backcrossing, as well as directly into a plant, are those that, in some embodiments, are introduced by genetic transformation techniques. Genetic transformation may therefore be used to insert a selected transgene into the *Cannabis* of the invention or may, alternatively, be used for the preparation of transgenes which can be introduced by backcrossing. Methods for the transformation of plants, including *Cannabis*, are well known to those of skill in the art. Techniques which may be employed to genetically transform *Cannabis* include, but are not limited to, electroporation, microprojectile bombardment, *Agrobacterium*-mediated transformation, and direct DNA uptake by protoplasts.

In some embodiments, transformation by electroporation is performed using either friable tissues, such as a suspension culture of cells or embryogenic callus or, alternatively, using immature embryos or other organized tissue directly. In one embodiment, cell walls of the chosen cells are partially degraded e.g., by exposing them to pectin-degrading enzymes or mechanically wound tissues in a controlled manner. In another embodiment, protoplasts are used for electroporation transformation.

In other embodiments, nucleic acids are delivered to plant cells using microprojectile bombardment. Particles are coated with nucleic acids and delivered into cells by a propelling force. Exemplary particles include those comprised of tungsten, platinum, or gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

In some embodiments, DNA is delivered into plant cells by Biolistics Particle Delivery System, which can be used to propel particles coated with DNA or cells through a screen, such as a stainless steel or Nytex screen, onto a surface covered with target *Cannabis* cells.

In other embodiments, *Agrobacterium*-mediated transfer is used for introducing gene loci into *Cannabis* plant cells. Vectors for *Agrobacterium*-mediated gene transfer can have convenient multiple-cloning sites (MCS) flanked by a promoter and a polyadenylation site for direct expression of inserted polypeptide coding genes. The use of *Agrobacterium*-mediated plant integrating vectors to introduce DNA into plant cells are described in Fraley et al., "*The SEV System: A New Disarmed Ti Plasmid Vector System for Plant Transformation*," Nature Bio. Tech., 3(7):629-635 (1985) and U.S. Pat. No. 5,563,055, each of which is herein incorporated by reference in its entirety. Use of *Agrobacterium* in the context of *Cannabis* transformation has been described, for example, by Galin-Avila, A. et al., "*A novel and rapid method for Agrobacterium-mediated production of stably transformed Cannabis sativa L. plants*," Industrial Crops and Products, 170:1-15, (2021), which is herein incorporated by reference in its entirety.

In other embodiments, genome editing methods known in the art such as, for example, use of CRISPR-Cas systems, zinc-finger nucleases (ZFNs), and transcription activator-like effector nucleases (TALENs) can be used to make site-specific modification of the plant genome.

Numerous herbicide tolerance genes are known in the art and, in some embodiments, may be employed with the invention. A non-limiting example is a gene conferring tolerance to imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., EMBO J., 7:1241, 1988; Gleen et al., Plant Molec. Biology, 18:1185, 1992; and Miki et al., Theor. Appl. Genet., 80:449, 1990, each of which is herein incorporated by reference in its entirety. In one embodiment, as a non-limiting example, a gene may be employed to confer tolerance to the exemplary sulfonylurea herbicide nicosulfuron.

Tolerance genes for glyphosate (tolerance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. U.S. Pat. No. 4,940,835, which discloses the nucleotide sequence of a form of EPSPS that can confer glyphosate tolerance, is herein incorporated by reference in its entirety.

In other embodiments, a plant of the invention can be transformed with a cloned tolerance gene to engineer plants that are tolerant to specific pathogen strains. See, for example Jones et al. (Science, 266:789-793, 1994) (cloning of the tomato Cf-9 gene for tolerance to *Cladosporium flavum*); Martin et al. (Science, 262:1432-1436, 1993) (tomato Pto gene for tolerance to *Pseudomonas syringae* pv); and Mindrinos et al. (Cell, 78(6):1089-1099, 1994) (*Arabidopsis* RPS2 gene for tolerance to *Pseudomonas syringae*).

In one embodiment, the accumulation of viral coat proteins in transformed plant cells imparts tolerance to viral infection and/or disease development effected by the virus from which the coat protein gene is derived and related viruses. See e.g., Beachy et al. (Ann. Rev. Phytopathol., 28:451, 1990). In another embodiment, a virus-specific antibody may also be used. See, for example, Tavladoraki et al. (Nature, 366:469-472, 1993) describing that transgenic plants expressing recombinant antibody genes are protected from virus attack.

In other embodiments, a plant of the invention comprises a tolerance gene to engineer plants that are tolerant to pests such as, for example, insects. Examples of pests of *Cannabis* plants are described in McPartland, J. M., "*Cannabis* pests," J. Internatl. Hemp Assoc. 3(2):49, 52-55 (1996).

One example of an insect tolerance gene includes a *Bacillus thuringiensis* protein and derivatives thereof. See, for example, Geiser et al. (Gene, 48(1):109-118, 1986) describing cloning and nucleotide sequence of a *Bacillus thuringiensis* delta-endotoxin gene. Moreover, DNA molecules encoding delta-endotoxin genes can be purchased from the American Type Culture Collection, Manassas, Va., for example, under ATCC Accession Nos. 40098, 67136, 31995 and 31998. A vitamin-binding protein may also be used, such as, for example, avidin. Yet another insect tolerance gene is an enzyme inhibitor, for example, protease, proteinase, or amylase inhibitors. See, for example, Abe et al. (J. Biol. Chem., 262:16793-16797, 1987) describing the nucleotide sequence of a rice cysteine proteinase inhibitor; Linthorst et al. (Plant Molec. Biol., 21:985-992, 1993) describing the nucleotide sequence of a cDNA encoding tobacco proteinase inhibitor I; and Sumitani et al. (Biosci. Biotech. Biochem., 57:1243-1248, 1993) describing the nucleotide sequence of a *Streptomyces nitrosporeus* alpha-amylase inhibitor. In other embodiments, an insect-specific hormone or pheromone may also be used. See, for example, the disclosure by Hammock et al. (Nature, 344:458-461, 1990) of baculovirus expression of cloned juvenile hormone esterase, an inactivator of juvenile hormone; Gade and Goldsworthy (Eds. Physiological System in Insects, Elsevier Academic Press, Burlington, Mass., 2007), describing allostatins and their potential use in pest control; and Palli et al. (Vitam. Horm., 73:59-100, 2005), disclosing use of ecdysteroid and ecdysteroid receptor in agriculture. The diuretic hormone receptor (DHR) was identified in Price et al. (Insect Mol. Biol., 13:469-480, 2004) as another potential candidate target of insecticides. Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994) describing enzymatic inactivation in transgenic tobacco via production of single-chain antibody fragments. Numerous other examples of insect tolerance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241, each of which is herein incorporated by reference in its entirety.

In other embodiments, plants of the *Cannabis* hybrid ADAM can comprise a genetic locus capable of restoring male fertility.

Examples of male-sterility genes and corresponding restorers which could be employed with the plants of the invention are known to those of skill in the art of plant breeding, see, for example, U.S. Pat. Nos. 5,530,191 and 5,684,242, the disclosures of which are each specifically incorporated herein by reference in their entirety. For example, in some embodiments, when cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, and all of the progeny are male sterile, as the CMS cytoplasm is derived from the female parent. In some embodiments, these male sterile plants can then be efficiently employed as the female parent in hybrid crosses with the restorer line.

In other embodiments, genes may be used conferring modified fatty acid metabolism. For example, Monika Bielecka, M., et al., Plant Biotechnology Journal, 12(5):613-623 (2014) describes targeted mutation of delta 12 and delta 15 desaturase genes in hemp produce major alterations in seed fatty acid composition including a high oleic hemp oil. In some embodiments, stearyl-ACP desaturase genes may be used, see Knutzon et al. (Proc. Natl. Acad. Sci. USA, 89:2624-2628, 1992). Modified fatty acid content is also disclosed in, for example, U.S. Pat. Nos. 6,828,475; 6,822,141; 6,770,465; 6,706,950; 6,660,849; 6,596,538; 6,589,767; 6,537,750; 6,489,461 and 6,459,018.

In other embodiments, a plant of the invention comprises a tolerance gene to abiotic stress. For example, delta-pyrroline-5-carboxylate synthetase (P5CS) from moth bean has been used to provide protection against general osmotic stress. Mannitol-1-phosphate dehydrogenase (mt1D) from *E. coli* has been used to provide protection against drought and salinity. Choline oxidase from *Arthrobactor globiformis* can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levansucrase (SacB) from yeast and *Bacillus subtilis*, respectively, can provide protection against drought. Overexpression of superoxide dismutase can be used to protect against superoxides, see U.S. Pat. No. 5,538,878.

In another embodiment, another trait that may find use with the *Cannabis* plants of the invention is a sequence which allows for site-specific recombination. Examples of such sequences include the FRT sequence used with the FLP recombinase (Zhu and Sadowski, J. Biol. Chem., 270:23044-23054 (1995)) and the LOX sequence used with CRE recombinase (Sauer, Mol. Cell. Biol., 7:2087-2096 (1987)).

In other aspects, the present invention provides a seed that produces the plant of *Cannabis* hybrid ADAM further comprising the single locus conversion, wherein said plant otherwise comprises all of the morphological and physiological characteristics of said *Cannabis* hybrid ADAM.

In some embodiments, the single locus conversion comprises a transgene. In one embodiment, the single locus comprises a nucleic acid sequence that enables site-specific genetic recombination or confers a trait of herbicide tolerance, insect tolerance, pest tolerance, disease tolerance, abiotic stress tolerance, or male sterility. In another embodiment, the single locus that confers herbicide tolerance confers tolerance to benzonitrile herbicides, cyclohexanedione herbicides, imidazolinone herbicides, phenoxy herbicides, sulfonylurea herbicides, triazine herbicides, 1-aminocyclopropane-1-carboxylic acid synthase-inhibiting herbicides, 4-hydroxyphenylpyruvate dioxygenase-inhibiting herbicides, acetolactate synthase-inhibiting herbicides, protoporphyrinogen oxidase-inhibiting herbicides, 2,4-dichlorophenoxyacetic acid (2,4-D), bromoxynil, dicamba, glufosinate, glyphosate, nicosulfuron, or quizalofop-p-ethyl.

In other aspect, the present invention provides tissue cultures of the plants of the invention including a tissue culture of *Cannabis* hybrid ADAM. In one embodiment, a composition comprises isolated cells of the same or a different type or a collection of such cells organized into parts of a plant. Exemplary types of tissue cultures are protoplasts, calli, and plant cells that are intact in plants or parts of plants, such as embryos, pollen, flowers, leaves, meristems, roots, root tips, anthers, and the like. In one embodiment, the tissue culture comprises embryos, protoplasts, meristematic cells, pollen, leaves, or anthers. Exemplary procedures for preparing tissue cultures of regenerable *Cannabis* cells and regenerating *Cannabis* plants therefrom are disclosed in U.S. Pat. Nos. 4,992,375; 5,015,580; 5,024,944; and 5,416,011, each of which are specifically incorporated herein by reference in their entirety.

In other aspects, the present invention provides a method of producing a commodity plant product, the method comprising producing the commodity plant product (i) from the plant of *Cannabis* hybrid ADAM; or (ii) from a plant of *Cannabis* hybrid ADAM further comprising a single locus conversion, wherein said plant otherwise comprises all of the morphological and physiological characteristics of said *Cannabis* hybrid.

Commodity plant products (e.g., any composition or product that is comprised of material derived from a plant, seed, plant cell, or plant part of the present invention) may be sold to consumers and can be viable or nonviable. Nonviable commodity products include, but are not limited to, nonviable seeds; processed seeds, seed parts, and plant parts; dehydrated plant tissue, frozen plant tissue, and processed plant tissue; seeds and plant parts processed for consumption, oil, tea, coffee, and any other drink or food for human or animal consumption; extracts; and raw material in industry.

In one embodiment, the commodity plant product is *Cannabis* oil extracted from the plant, seed, plant cell, or plant part of the present invention. In another embodiment, the commodity plant product comprises at least one cell of *Cannabis* hybrid ADAM.

EXAMPLES

Example 1

Development of *Cannabis* Hybrid ADAM

Breeding History:

*Cannabis* hybrid ADAM has superior characteristics. The female (line AD-JL-0001) and male (line BD-AL-0001) parents were crossed to produce hybrid ($F_1$) seeds of ADAM. The seeds of ADAM can be grown to produce hybrid plants and parts thereof. The hybrid ADAM can be propagated by seeds produced from crossing line AD-JL0001 with line BD-AL-0001, or vegetatively.

The origin and breeding history of hybrid plant ADAM can be summarized as follows: the line AD-JL-0001 (a proprietary line owned by Applicant) was used as the female plant and crossed by pollen from the line BD-AL-0001 (a proprietary line owned by Applicant). The first trial planting of this *Cannabis* hybrid ADAM was done in San Jose, California, U.S.A., in the summer of the first year. Lines AD-JL-0001 and BD-AL-0001 have never been publicly available.

The line AD-JL-0001 is a pure Jamaican Landrace *sativa* cultivar used as the female parent in this cross. The line AD-JL-0001 has good performance in seed production; thin leaf, indeterminate; narrow leaflets; tall, up to 2 to 6 meters (6 to 18 feet), laxly branched; flowers radiate a sweet floral smell that is herbal, peppery, spice, citrus, floral, and minty; and has the following terpene profile: b-Myrcene of about 40%, b-Caryophyllene of about 17%, a-Bisabolol of about 6%, a-Humulene of about 5%, d-Limonene of about 4%, b-Ocimene of about 4%, Linalool of about 2%, isopulegol of about 2%, a-Pinene of about 1%, b-Pinene of about 1%. Qualitative results of chemical extractions performed on the leaf presses of line AD-JL-0001 are shown in Tables 1 and 2.

TABLE 1

| Cannabinoid chemical profile. | | | | |
|---|---|---|---|---|
| Cannabinoid | [1]K051 Black Domina (Reference Flower A) | [2]BD-AL-0001 | [1]Jamaican (Reference Flower)1 | [2]AD-JL-0001 |
| CBDV | Absence | Absence | Absence | Absence |
| CBDVA | Absence | Absence | Absence | Absence |
| THCV | Absence | Absence | Absence | Absence |
| CBD | Absence | Absence | Absence | Absence |
| CBG | Presence | Absence | Presence | Absence |
| CBDA | Low Level | Absence | Absence | Absence |
| CBGA | Presence | Presence | Presence | Presence |
| CBN | Absence | Absence | Absence | Absence |
| THCVA | Presence | Presence | Presence | Absence |
| THC | Presence | Presence | Absence | Absence |
| D8THC | Absence | Absence | Absence | Absence |
| CBL | Absence | Absence | Absence | Absence |
| CBC | Absence | Absence | Absence | Absence |
| CBNA | Presence | Presence | Presence | Presence |
| THCA | Presence | Presence | Presence | Presence |
| CBLA | Absence | Absence | Absence | Absence |
| CBCA | Presence | Presence | Presence | Presence |

[1]Chemical extraction data from flower.
[2]Chemical extractions performed on leaf presses.

TABLE 2

| Cannabinoid ratios. | | | | |
|---|---|---|---|---|
| Ratio | [1]K051 Black Domina (Reference Flower A) | [2]BD-AL-0001 | [1]Jamaican (Reference Flower)1 | [2]AD-JL-0001 |
| THCA:CBGA | 10.94 | 2.86 | 8.07 | 4.36 |
| CBCA:CBGA | 0.21 | 6.85 | 0.13 | 1.86 |
| THCA:CBCA | 51.51 | 0.42 | 62.91 | 2.35 |

[1]Chemical extraction data from flower.
[2]Chemical extractions performed on leaf presses.

The line BD-AL-0001 is a pure Afghani Landrace indica cultivar used as the male parent in this cross. The line BD-AL-0001 has fat, determinate, dark green leaves having 5 to 9 very wide, coarsely serrated leaflets in a circular array; plants usually small, 1.2 meters (4 feet) or less, not laxly branched; a skunky acrid smell; and has the qualitative chemical profile and ratios shown in Tables 1 and 2.

*Cannabis* hybrid ADAM has shown uniformity and stability for traits, within the limits of environmental influence for the traits as described in the following descriptive information. *Cannabis* hybrid ADAM has the following morphologic and other characteristics: breeds true; hybrid vigor (expressed through its increased plant weight and size); hollow stems without fiber in the middle; dark green leaf color; large, round and mottled seeds; radiates a mix of sweet floral smell from Jamaican side and a skunky acrid smell from its Afghan side a perfect blend (e.g., smells skunky, clove, sour, earthy, pine, floral, sweet, minty); THC content of about 15%; carried the genetic cannabinoid component THCV from its Afghan father and has the following terpene profile: b-Myrcene of about 27%, a-Pinene of about 8%, d-Limonene of about 7%, a-Bisabolol of about 7%, b-Pinene of about 5%, b-Caryophyllene of about 4%, b-Ocimene of about 3%, Linalool of about 3%, Isopulegol of about 2%, Camphene of about 1%, a-Humulene of about 1%.

Example 2

Cannabinoid and Terpene Profiles

Cannabinoid and terpene profiles of *Cannabis* hybrid ADAM and its female parent line AD-JL-0001 were determined by high performance liquid chromatography (HPLC). The cannabinoid and terpene profiles of female parent line AD-JL-0001 are shown in Tables 3 and 4, respectively; and the cannabinoid and terpene profiles of *Cannabis* hybrid ADAM are shown in Tables 5 and 6, respectively.

TABLE 3

Cannabinoid profile of line AD-JL-0001.

| Cannabinoid | Percent | mg/g | LOQ (mg/g) | LOD (mg/g) |
|---|---|---|---|---|
| d9-THC | 0.64 | 6.44 | 1.00 | 0.33 |
| d8-THC | ND | ND | 1.00 | 0.33 |
| THCA | 15.76 | 157.65 | 1.00 | 0.33 |
| THCV | ND | ND | 1.00 | 0.33 |
| THCVA | ND | ND | 1.00 | 0.33 |
| CBC | ND | ND | 1.00 | 0.33 |
| CBG | ND | ND | 1.00 | 0.33 |
| CBGA | 1.41 | 14.05 | 1.00 | 0.33 |
| CBN | ND | ND | 1.00 | 0.33 |
| CBD | ND | ND | 1.00 | 0.33 |
| CBDV | ND | ND | 1.00 | 0.33 |
| CBDA | ND | ND | 1.00 | 0.33 |
| Total | 17.81 | 178.140 | | |
| Total THC | 14.46 | 144.70 | | |
| Total CBD | <LOQ | <1 mg/g | | |

Sample type: Flower
Moisture: 11.3%
ND: Not Detected
Approximately 4% Decarboxylated THC
Total THC = ((THCA * 0.877) + d9-THC)
Total CBD = ((CBDA * 0.877) + CBD)

TABLE 4

Terpene profile of line AD-JL-0001.

| Terpene | Percent | mg/g | LOQ (mg/g) | LOD (mg/g) |
|---|---|---|---|---|
| a-Pinene | 0.01 | 0.07 | 0.02 | 0.06 |
| Camphene | ND | 0.00 | 0.02 | 0.07 |
| b-Myrcene | 0.40 | 3.52 | 0.02 | 0.03 |
| b-Pinene | 0.01 | 0.07 | 0.02 | 0.05 |
| d3-Carene | ND | 0.00 | 0.02 | 0.04 |
| a-Terpinene | ND | 0.00 | 0.02 | 0.04 |
| a-Ocimene | ND | 0.00 | 0.06 | 0.02 |
| d-Limonene | 0.04 | 0.34 | 0.02 | 0.03 |
| p-Cymene | ND | 0.00 | 0.02 | 0.04 |
| b-Ocimene | 0.04 | 0.35 | 0.14 | 0.04 |
| g-Terpinene | ND | 0.00 | 0.02 | 0.06 |
| Terpinolene | ND | 0.00 | 0.02 | 0.05 |
| Linalool | 0.02 | 0.16 | 0.02 | 0.05 |
| Isopulegol | 0.02 | 0.15 | 0.02 | 0.07 |
| Geraniol | ND | 0.00 | 0.02 | 0.07 |
| b-Caryophyllene | 0.17 | 1.54 | 0.02 | 0.01 |
| a-Humulene | 0.05 | 0.41 | 0.02 | 0.06 |
| cis-Nerolidol | ND | 0.00 | 0.08 | 0.03 |
| trans-Nerolidol | ND | 0.00 | 0.12 | 0.01 |
| guaiol | ND | 0.00 | 0.2 | 0.03 |
| a-Bisabolol | 0.06 | 0.57 | 0.2 | 0.02 |
| Total Terpenes | 0.8 | | | |

ND: Not Detected

TABLE 5

Cannabinoid profile of *Cannabis* hybrid ADAM.

| Cannabinoid | Percent | mg/g | LOQ (mg/g) | LOD (mg/g) |
|---|---|---|---|---|
| d9-THC | 0.43 | 4.27 | 1.00 | 0.33 |
| d8-THC | ND | ND | 1.00 | 0.33 |
| THCA | 14.17 | 141.67 | 1.00 | 0.33 |
| THCV | ND | ND | 1.00 | 0.33 |
| THCVA | 0.18 | 1.75 | 1.00 | 0.33 |
| CBC | ND | ND | 1.00 | 0.33 |
| CBG | ND | ND | 1.00 | 0.33 |
| CBGA | 0.72 | 7.24 | 1.00 | 0.33 |
| CBN | ND | ND | 1.00 | 0.33 |
| CBD | ND | ND | 1.00 | 0.33 |
| CBDV | ND | ND | 1.00 | 0.33 |
| CBDA | ND | ND | 1.00 | 0.33 |
| Total | 15.50 | 154.930 | | |
| Total THC | 12.86 | 128.51 | | |
| Total CBD | <LOQ | <1 mg/g | | |

Sample type: Flower
Moisture: 13.7%
ND: Not Detected
Approximately 3% Decarboxylated THC
Total THC = ((THCA * 0.877) + d9-THC)
Total CBD = ((CBDA * 0.877) + CBD)

TABLE 6

Terpene profile of *Cannabis* hybrid ADAM.

| Terpene | Percent | mg/g | LOQ (mg/g) | LOD (mg/g) |
|---|---|---|---|---|
| a-Pinene | 0.08 | 0.69 | 0.02 | 0.06 |
| Camphene | 0.01 | 0.05 | 0.02 | 0.07 |
| b-Myrcene | 0.27 | 2.36 | 0.02 | 0.03 |
| b-Pinene | 0.05 | 0.4 | 0.02 | 0.05 |
| d3-Carene | ND | 0.00 | 0.02 | 0.04 |
| a-Terpinene | ND | 0.00 | 0.02 | 0.04 |
| a-Ocimene | ND | 0.00 | 0.06 | 0.02 |
| d-Limonene | 0.07 | 0.62 | 0.02 | 0.03 |
| p-Cymene | ND | 0.00 | 0.02 | 0.04 |
| b-Ocimene | 0.03 | 0.27 | 0.14 | 0.04 |
| g-Terpinene | ND | 0.00 | 0.02 | 0.06 |
| Terpinolene | ND | 0.00 | 0.02 | 0.05 |
| Linalool | 0.03 | 0.2816 | 0.02 | 0.05 |
| Isopulegol | 0.02 | 0.18 | 0.02 | 0.07 |
| Geraniol | ND | 0.00 | 0.02 | 0.07 |
| b-Caryophyllene | 0.04 | 0.36 | 0.02 | 0.01 |
| a-Humulene | 0.01 | 0.11 | 0.02 | 0.06 |
| cis-Nerolidol | ND | 0.00 | 0.08 | 0.03 |
| trans-Nerolidol | ND | 0.00 | 0.12 | 0.01 |
| guaiol | ND | 0.00 | 0.2 | 0.03 |
| a-Bisabolol | 0.07 | 0.56 | 0.2 | 0.02 |
| Total Terpenes | 0.7 | | | |

ND: Not Detected

DEPOSIT INFORMATION

A sample of the *Cannabis* hybrid ADAM seed of this invention has been deposited (625 seeds) with the ATCC, 10801 University Boulevard, Manassas, Va. 20110-2209, U.S.A. The date of deposit is May 5, 2023 and the number for those deposited seeds of *Cannabis* hybrid ADAM is ATCC Accession No. PTA-127583.

Applicant hereby make the following statements regarding the deposited *Cannabis* hybrid ADAM seed (deposited as ATCC Accession No. PTA-127583): (i) During the pendency of this application, access to the invention will be afforded to the Commissioner upon request; (ii) All restrictions on availability to the public will be irrevocably removed upon granting of the patent under conditions specified in 37 C.F.R. § 1.808; (iii) The deposit will be maintained in a public repository for a period of 30 years or 5 years after the last request or for the effective life of the patent, whichever is longer; (iv) A test of the viability of the biological material at the time of deposit will be conducted by the public depository under 37 C.F.R. § 1.807; and (v) The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same hybrid with the ATCC.

While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

Enumerated Embodiments

The following enumerated embodiments are provided, the numbering of which is not to be construed as designating levels of importance.

Embodiment 1 provides a plant of *Cannabis* hybrid ADAM, wherein representative seed of said hybrid have been deposited under ATCC Accession No. PTA-127583.

Embodiment 2 provides a plant part of the plant of embodiment 1, wherein the plant part comprises at least one cell of said plant.

Embodiment 3 provides a seed of *Cannabis* hybrid ADAM.

Embodiment 4 provides a method of producing a *Cannabis* seed, the method comprising crossing the plant of embodiment 1 with itself or a second *Cannabis* plant to produce said *Cannabis* seed.

Embodiment 5 provides the method of embodiment 4, wherein the second *Cannabis* plant is a nonisogenic *Cannabis* plant.

Embodiment 6 provides an $F_1$ *Cannabis* seed produced by the method of embodiment 4 or 5.

Embodiment 7 provides an $F_1$ *Cannabis* plant produced by growing the $F_1$ *Cannabis* seed of embodiment 6.

Embodiment 8 provides a plant of *Cannabis* hybrid ADAM further comprising a single locus conversion, wherein said plant otherwise comprises all of the morphological and physiological characteristics of said *Cannabis* hybrid ADAM.

Embodiment 9 provides the plant of embodiment 8, wherein the single locus conversion comprises a transgene.

Embodiment 10 provides a seed that produces the plant of embodiment 8.

Embodiment 11 provides the seed of embodiment 10, wherein the single locus comprises a nucleic acid sequence that enables site-specific genetic recombination or confers a trait.

Embodiment 12 provides the seed of embodiment 8, wherein the single locus conversion comprises a transgene.

Embodiment 13 provides the method of embodiment 5 further comprising:

(a) crossing a plant grown from said *Cannabis* seed with itself or a different *Cannabis* plant to produce seed of a progeny plant of a subsequent generation;

(b) growing a progeny plant of a subsequent generation from said seed of a progeny plant of a subsequent generation and crossing the progeny plant of a subsequent generation with itself or a second plant to produce seed of a progeny plant of a further subsequent generation; and (c) repeating step (b) with sufficient inbreeding to produce seed of an inbred *Cannabis* plant that is derived from *Cannabis* hybrid ADAM.

Embodiment 14 provides the method of embodiment 13 further comprising crossing a plant grown from said seed of an inbred *Cannabis* plant that is derived from *Cannabis* hybrid ADAM with a nonisogenic plant to produce seed of a hybrid *Cannabis* plant that is derived from *Cannabis* hybrid ADAM.

Embodiment 15 provides a composition comprising a plant seed growth media and the seed of embodiment 3, 6, 10, 11, or 12.

Embodiment 16 provides the composition of embodiment 15, wherein the plant seed growth media comprises a soil or a synthetic cultivation medium.

Embodiment 17 provides a method of producing a commodity plant product, the method comprising producing the commodity plant product from the plant of embodiment 1, 8, or 9.

Embodiment 18 provides a commodity plant product that is produced by the method of embodiment 17, wherein the commodity plant product comprises at least one cell of *Cannabis* hybrid ADAM.

Other Embodiments

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

I claim:

1. A plant of *Cannabis* hybrid ADAM, wherein representative seed of said hybrid have has been deposited under ATCC Accession No. PTA-127583.

2. A plant part of the plant of claim 1, wherein the plant part comprises at least one cell of said plant.

3. A seed of the plant of claim 1.

4. A method of producing a *Cannabis* seed, the method comprising crossing the plant of claim 1 with itself or a second *Cannabis* plant to produce said *Cannabis* seed.

5. The method of claim 4, wherein the second *Cannabis* plant is a nonisogenic *Cannabis* plant.

6. The method of claim 5 further comprising:

(a) crossing a plant grown from said *Cannabis* seed with itself or a different *Cannabis* plant to produce seed of a progeny plant of a subsequent generation;

(b) growing a progeny plant of a subsequent generation from said seed of a progeny plant of a subsequent generation and crossing the progeny plant of a subsequent generation with itself or a second plant to produce seed of a progeny plant of a further subsequent generation; and (c) repeating step (b) with sufficient inbreeding to produce seed of an inbred *Cannabis* plant that is derived from *Cannabis* hybrid ADAM.

7. The method of claim 6 further comprising crossing a plant grown from said seed of an inbred *Cannabis* plant that is derived from *Cannabis* hybrid ADAM with a nonisogenic plant to produce seed of a hybrid *Cannabis* plant that is derived from *Cannabis* hybrid ADAM.

8. A composition comprising a plant seed growth media and the seed of claim 3.

9. The composition of claim 8, wherein the plant seed growth media comprises a soil or a synthetic cultivation medium.

10. A method of producing a commodity plant product, the method comprising producing the commodity plant product from the plant of claim 1.

11. A commodity plant product that is produced by the method of claim 10, wherein the commodity plant product comprises at least one cell of the plant of *Cannabis* hybrid ADAM.

* * * * *